United States Patent
Li et al.

(10) Patent No.: US 10,487,046 B1
(45) Date of Patent: *Nov. 26, 2019

(54) DIHYDROXYTYROSOL HEXAMETHYLENE-1,6-DICARBAMATE HAVING ANTIOXIDANT ACTIVITY AND A METHOD OF PREPARING THE SAME

(71) Applicants: Han Li, Xi'an (CN); Yuzhi Liu, Xi'an (CN); Xingke Ju, Xi'an (CN); Lei Tian, Xi'an (CN); Juan Li, Xi'an (CN); Nan Hui, Xi'an (CN); Guaiping Qiao, Xi'an (CN); Ning Liu, Xi'an (CN); Liuyi Yang, Xi'an (CN); Xuefeng Chen, Xi'an (CN)

(72) Inventors: Han Li, Xi'an (CN); Yuzhi Liu, Xi'an (CN); Xingke Ju, Xi'an (CN); Lei Tian, Xi'an (CN); Juan Li, Xi'an (CN); Nan Hui, Xi'an (CN); Guaiping Qiao, Xi'an (CN); Ning Liu, Xi'an (CN); Liuyi Yang, Xi'an (CN); Xuefeng Chen, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,906

(22) Filed: Jul. 13, 2019

(30) Foreign Application Priority Data

May 6, 2019 (CN) .......................... 2019 1 0369370

(51) Int. Cl.
*C07C 233/09* (2006.01)
*C07C 231/06* (2006.01)

(52) U.S. Cl.
CPC .......... *C07C 233/09* (2013.01); *C07C 231/06* (2013.01)

(58) Field of Classification Search
CPC ........................... C07C 233/09; C07C 231/06
See application file for complete search history.

(56) References Cited

PUBLICATIONS

Unruh et al., Thermally activated, single component epoxy systems, (Macromolecules (Washington, DC, United States) (2011)44(16), 6318-6325).*

* cited by examiner

*Primary Examiner* — Jafar F Parsa

(57) ABSTRACT

A compound having the following formula I:

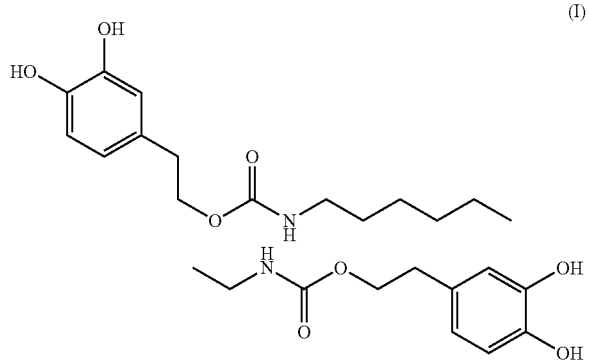

is disclosed. A method of preparing the compound of formula (I) is also disclosed.

11 Claims, 1 Drawing Sheet

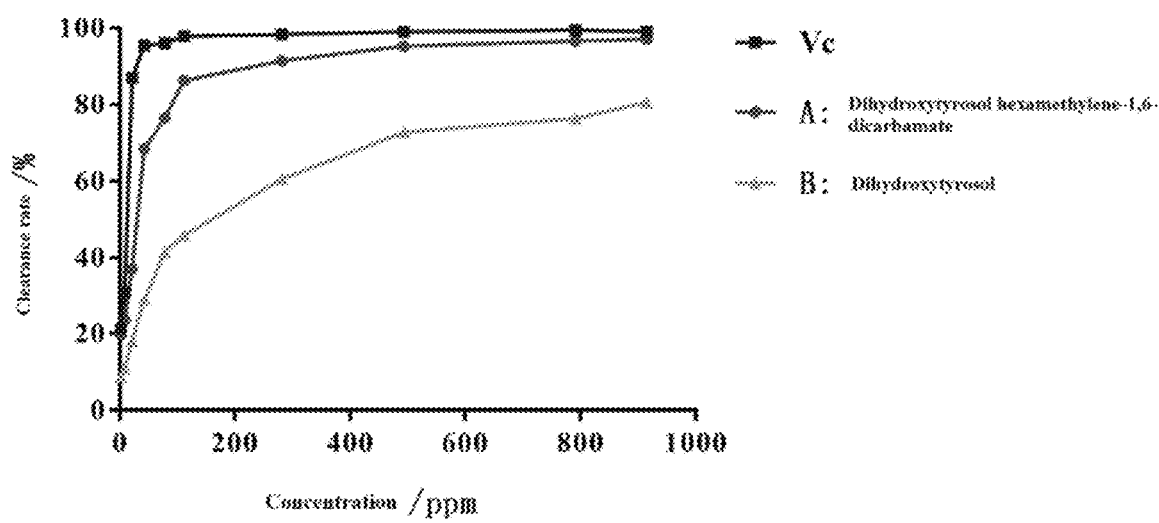

DIHYDROXYTYROSOL HEXAMETHYLENE-1,6-DICARBAMATE HAVING ANTIOXIDANT ACTIVITY AND A METHOD OF PREPARING THE SAME

The present invention claims priority to Chinese Patent Application No.: 201910369370.5, filed May 6, 2019, which is incorporated by reference for all purposes as if fully set forth herein.

FIELD OF THE INVENTION

The present invention relates to food and cosmetic additives, in particular, to dihydroxytyrosol hexamethylene-1,6-dicarbamate ((3,4-dihydroxyphenethyl) hexane-1,6-diyldicarbamate) having antioxidant activity and a method of preparing the same.

BACKGROUND OF THE INVENTION

Oxidation is the main cause of food spoilage. During storage and transportation, foods are spoiled and degraded by microorganisms. Foods also chemically react with oxygen in the air, causing them, especially oils or fats, to deteriorate. This not only reduces food nutrition, but also deteriorates flavor and color. This also produces harmful substances that endanger human health. Therefore, adding an appropriate amount of antioxidants to foods is a simple and economical method to prevent oxidative deterioration of foods.

The use of antioxidants not only prolongs the storage period and the shelf life of foods, but also brings good economic benefits to producers and distributors and gives consumers a better sense of security. At present, synthetic and semi-synthetic antioxidants have attracted more and more attentions. In addition to being used alone, the antioxidants can also be used with other food additives having other functions to form a multifunctional preparation and a dosage form, for example, packaging materials with preservatives and antioxidants.

Hydroxytyrosol (4-(2-hydroxyethyl)-1,2-benzenediol; compound of formula II) is a phenylethanoid, a type of phenolic phytochemical with antioxidant properties in vitro. In nature, hydroxytyrosol is found in olive leaf and olive oil, in the form of its elenolic acid ester oleuropein and, especially after degradation, in its plain form.

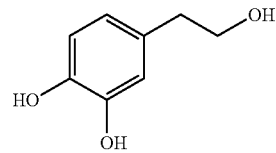

1,6-Hexamethylene diisocyanate (HDI, compound of formula III) has excellent UV absorption capacity, and it is an important raw material for synthetic polyurethane. Because HDI does not have the structural characteristics of C=C and benzene ring, the polyurethane prepared from HDI has yellowing resistance and high decorative properties, widely used in coatings, adhesives, synthetic leather and other fields.

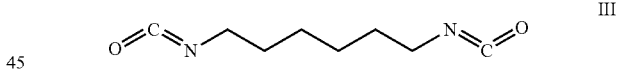

SUMMARY OF THE INVENTION

In one embodiment, the present invention provides a compound having the following formula I:

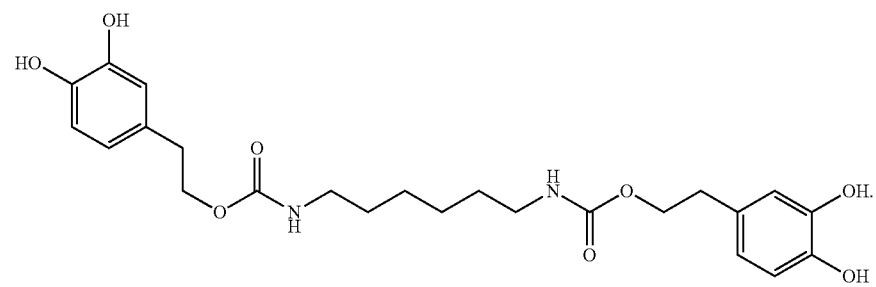

In another embodiment, the present invention provides a method of preparing the compound of formula I. The method includes: reacting the compound of formula II with the compound of formula III to obtain the compound of formula I:

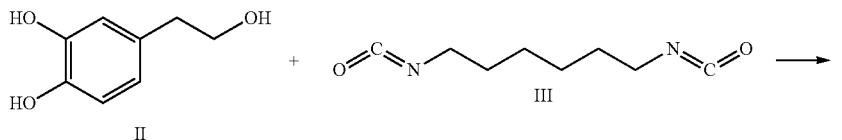

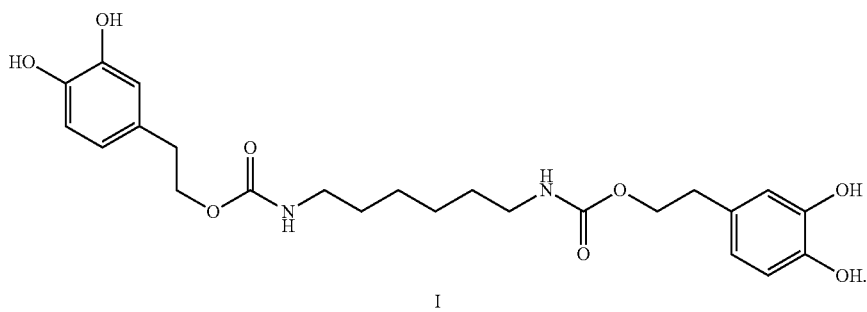

In another embodiment, the reaction of the compound of formula II with the compound of formula III includes the following steps: dissolving the compound of formula II and a catalyst in an organic solvent to form a reaction mixture under nitrogen atmosphere; adding the compound of formula III to the reaction mixture; heating the reaction mixture at 60-108° C. for 6-10 hours; removing the organic solvent from the reaction mixture to obtain a crude product; and purifying the crude product by silica gel flash chromatography with a mixture of petroleum ether and ethyl acetate as an eluent.

In another embodiment, the organic solvent is toluene, DMF, or acetonitrile.

In another embodiment, the organic solvent is toluene.

In another embodiment, the molar ratio of the compound of formula II and the compound of formula III is 2.5:1 to 3:1.

In another embodiment, the molar ratio of the compound of formula II and the compound of formula III is 3:1.

In another embodiment, the catalyst is triethylamine or DMAP.

In another embodiment, the catalyst is DMAP.

In another embodiment, the reaction mixture is heated at 108° C.

In another embodiment, the reaction mixture is heated for 8 hours.

In another embodiment, the mixture of petroleum ether and ethyl acetate has a volume ratio of 5:1.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the DPPH Radical Scavenging Activities of Vitamin C (Vc), dihydroxytyrosol hexamethylene-1,6-dicarbamate (A), and hydroxytyrosol (B).

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

In the present invention, hydroxytyrosol was structurally modified by reacting with 1,6-hexamethylene diisocyanate to obtain dihydroxytyrosol hexamethylene-1,6-dicarbamate. The synthesis method of dihydroxytyrosol hexamethylene-1,6-dicarbamate is described. The antioxidant activity of dihydroxytyrosol hexamethylene-1,6-dicarbamate was also measured. Dihydroxytyrosol hexamethylene-1,6-dicarbamate can be used as a new type of antioxidant additive for food, medicine and health care products.

Example 1

Preparation of dihydroxytyrosol hexamethylene-1,6-dicarbamate (bis(3,4-dihydroxyphenethyl) hexane-1,6-diyldicarbamate) (Formula I)

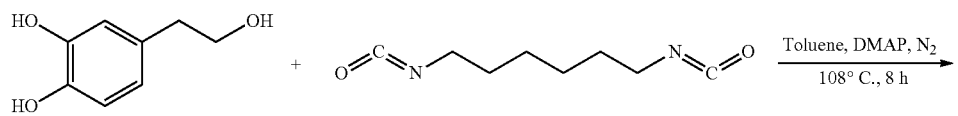

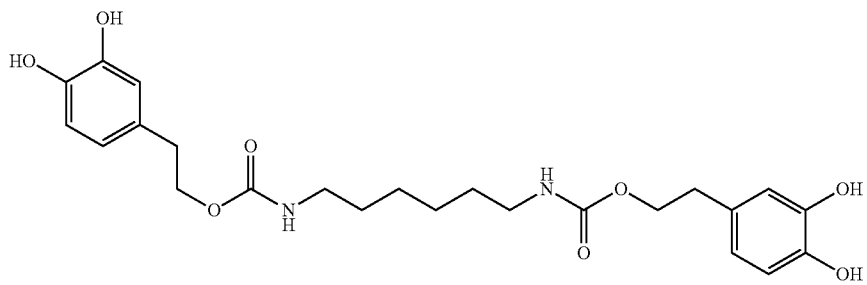

139 mg (0.90 mmol) hydroxytyrosol and 3.7 mg (0.03 mmol) DMAP (4-dimethylaminopyridine) were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 108° C. under nitrogen atmosphere for 8 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 62.26 mg purified dihydroxytyrosol hexamethylene-1,6-dicarbamate, a yield of 43.55%.

$^1$H-NMR (400 MHz, DMSO-$d_6$) δ (ppm): 88.43-7.62 (2H, br), 6.90 (2H, s), 6.86~6.60 (4H, m), 5.70 (4H, m), 4.72 (4H, m), 3.35-2.90 (8H, m), 1.58-1.15 (8H, m); $^{13}$C-NMR (75 MHz, DMSO-$d_6$) δ (ppm): 158.6, 148.9, 145.0, 136.7, 122.6, 119.5, 117.3, 64.1, 45.7, 36.3, 28.2; MS (ESI) for (M+H)$^+$: 477.2.

Example 2

Preparation of dihydroxytyrosol hexamethylene-1,6-dicarbamate (bis(3,4-dihydroxyphenethyl) hexane-1,6-diyldicarbamate) (Formula I)

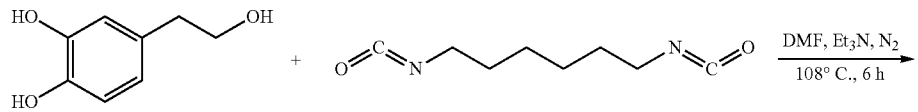

-continued

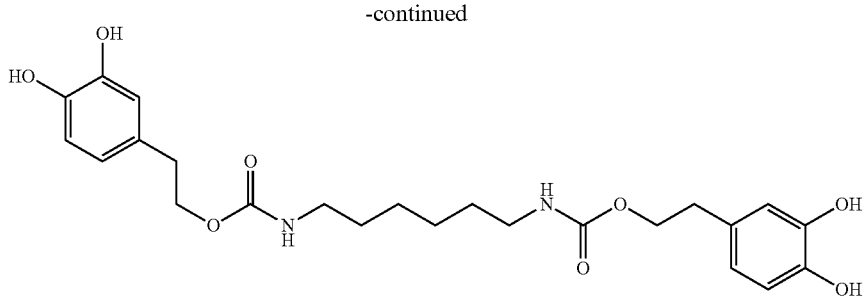

139 mg (0.90 mmol) hydroxytyrosol and 42 µL (0.30 mmol) triethylamine were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 108° C. under nitrogen atmosphere for 8 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 53.18 mg purified dihydroxytyrosol hexamethylene-1,6-dicarbamate, a yield of 37.20%.

Example 3

Preparation of dihydroxytyrosol hexamethylene-1,6-dicarbamate (bis(3,4-dihydroxyphenethyl) hexane-1,6-diyldicarbamate) (Formula I)

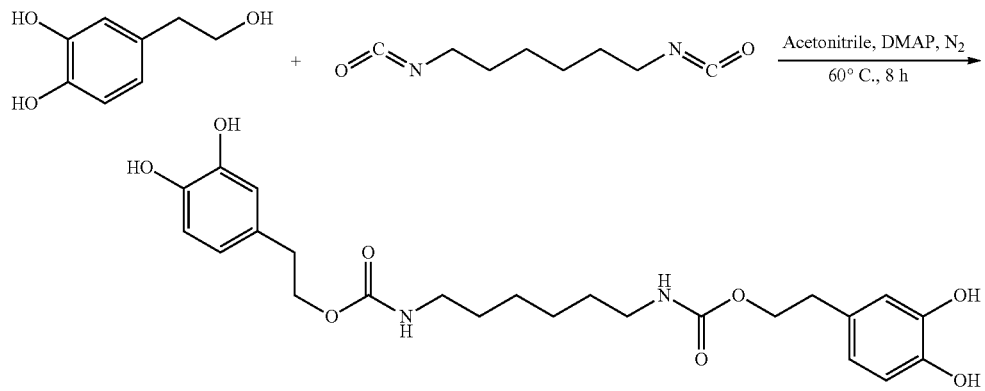

1 ml 6 g (0.75 mmol) hydroxytyrosol and 3.7 mg (0.03 mmol) DMAP (4-dimethylaminopyridine) were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 60° C. under nitrogen atmosphere for 8 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 56.47 mg purified dihydroxytyrosol hexamethylene-1,6-dicarbamate, a yield of 39.50%.

Example 4

Preparation of dihydroxytyrosol hexamethylene-1,6-dicarbamate (bis(3,4-dihydroxyphenethyl) hexane-1,6-diyldicarbamate) (Formula I)

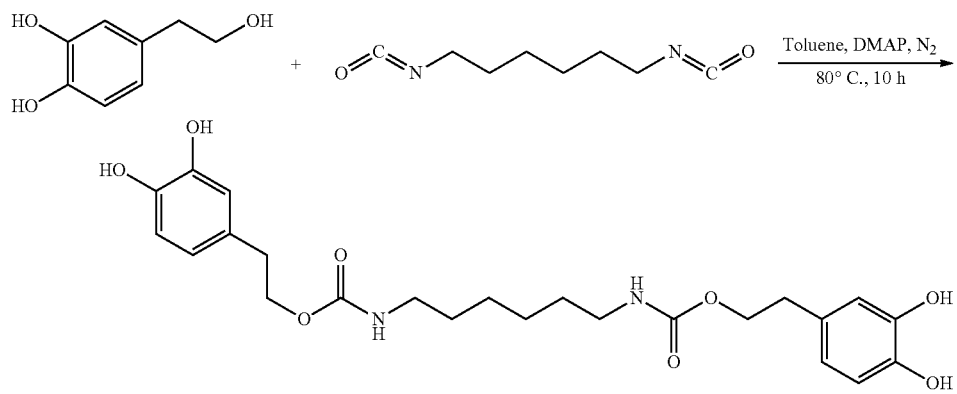

116 mg (0.75 mmol) hydroxytyrosol and 3.7 mg (0.03 mmol) DMAP (4-dimethylaminopyridine) were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 80° C. under nitrogen atmosphere for 10 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 44.29 mg purified dihydroxytyrosol hexamethylene-1,6-dicarbamate, a yield of 30.98%.

Example 5

Preparation of dihydroxytyrosol hexamethylene-1,6-dicarbamate (bis(3,4-dihydroxyphenethyl) hexane-1,6-diyldicarbamate) (Formula I)

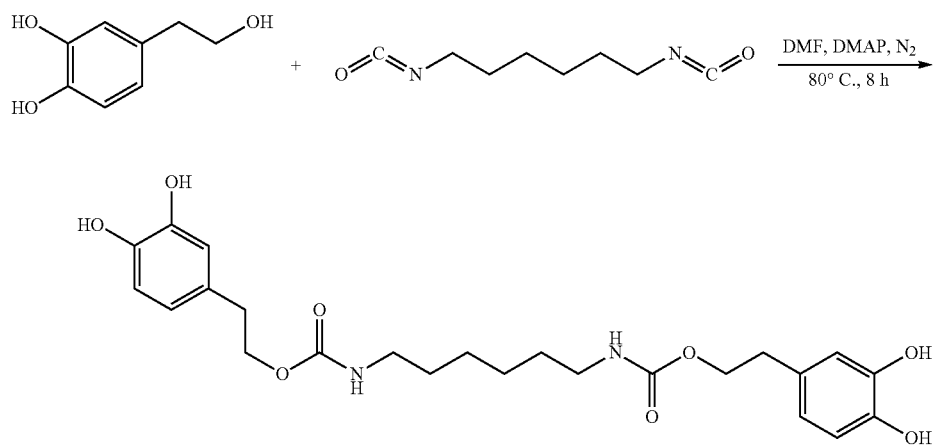 [SMILES: OCCc1ccc(O)c(O)c1 ; O=C=NCCCCCCN=C=O ; O=C(NCCCCCCNC(=O)OCCc1ccc(O)c(O)c1)OCCc1ccc(O)c(O)c1]

139 mg (0.90 mmol) hydroxytyrosol and 3.7 mg (0.03 mmol) DMAP (4-dimethylaminopyridine) were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 80° C. under nitrogen atmosphere for 8 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 57.41 mg purified dihydroxytyrosol hexamethylene-1,6-dicarbamate, a yield of 40.16%.

Example 6

Preparation of dihydroxytyrosol hexamethylene-1,6-dicarbamate (bis(3,4-dihydroxyphenethyl) hexane-1,6-diyldicarbamate) (Formula I)

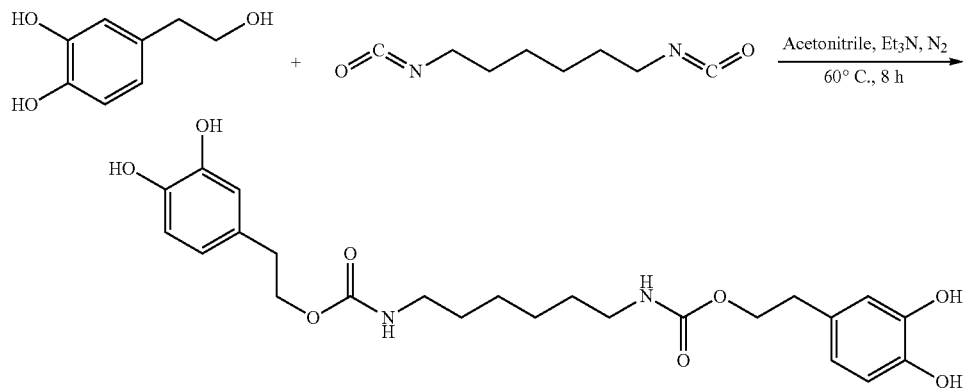

139 mg (0.90 mmol) hydroxytyrosol and 42 μL (0.30 mmol) triethylamine were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 60° C. under nitrogen atmosphere for 8 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 50.38 mg purified dihydroxytyrosol hexamethylene-1,6-dicarbamate, a yield of 35.24%.

Example 7

Preparation of dihydroxytyrosol hexamethylene-1,6-dicarbamate (bis(3,4-dihydroxyphenethyl) hexane-1,6-diyldicarbamate) (Formula I)

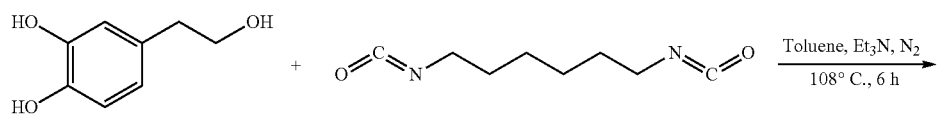

-continued

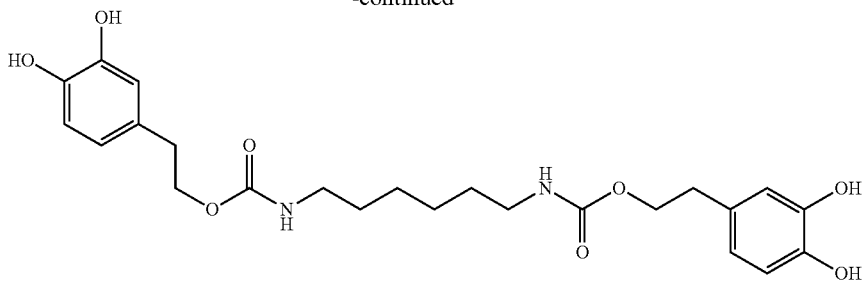

116 mg (0.75 mmol) hydroxytyrosol and 42 μL (0.30 mmol) triethylamine were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 108° C. under nitrogen atmosphere for 6 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 41.55 mg purified dihydroxytyrosol hexamethylene-1,6-dicarbamate, a yield of 29.08%.

Example 8

Preparation of dihydroxytyrosol hexamethylene-1,6-dicarbamate (bis(3,4-dihydroxyphenethyl) hexane-1,6-diyldicarbamate) (Formula I)

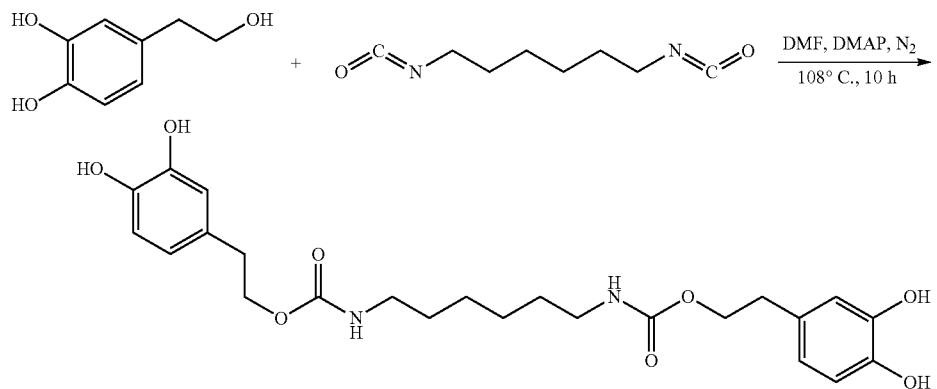

139 mg (0.90 mmol) hydroxytyrosol and 3.7 mg (0.03 mmol) DMAP (4-dimethylaminopyridine) were placed in a 100 mL reactor. 50 mL toluene was added to form a reaction mixture under nitrogen atmosphere. 50 mg (0.30 mmol) 1,6-hexamethylene diisocyanate in 5 mL toluene was added slowly to the reaction mixture. The reaction mixture was heated at 108° C. under nitrogen atmosphere for 10 hours. After thin layer chromatography (TLC) indicated that the reaction was complete, the reaction mixture was cooled down to room temperature, concentrated under reduced pressure to obtain a crude product. The crude product was purified by silica gel flash chromatography eluting with a mixture of petroleum ether and ethyl acetate (5:1, v/v). The elution was collected and concentrated to obtain 52.72 mg purified dihydroxytyrosol hexamethylene-1,6-dicarbamate, a yield of 36.88%.

Example 9

DPPH Radical Scavenging Activity Assay

Experimental Principle 2,2-Diphenyl-1-picryl hydrazyl (DPPH) is an organic compound composed of a stable organic radical. In the DPPH molecule, due to the presence of multiple electron-withdrawing —$NO_2$ and large it bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Experimental Method (a) Preparation of DPPH solution: measuring exact amount of 2,2-diphenyl-1-picryl hydrazyl (DPPH) and dissolving in methanol to prepare a $0.2 \times 10^{-4}$ mol/L DPPH solution, stored at 0° C. in dark.

(b) Preparation of sample solutions: Vc (vitamin C, positive control), dihydroxytyrosol hexamethylene-1,6-dicarbamate, and hydroxytyrosol (control) were dissolved in methanol and diluted in a concentration gradient. The sample solutions are shown in Table 1.

TABLE 1

Sample Solutions

| No. | Samples | Concentrations (μg/ml) |
|---|---|---|
| Vc | Vitamin C | 1.76, 8.80, 21.12, 42.24, 79.20, 112.64, 281.60, 492.80, 792.00, 915.20 |
| A | dihydroxytyrosol hexamethylene-1,6-dicarbamate | 1.76, 8.80, 21.12, 42.24, 79.20, 112.64, 281.60, 492.80, 792.00, 915.20 |
| B | hydroxytyrosol | 1.76, 8.80, 21.12, 42.24, 79.20, 112.64, 281.60, 492.80, 792.00, 915.20 |

(c) Specific steps:

Measuring the scavenging activity of the sample solutions: 2 mL of the sample solutions (table 1) at each concentration gradient was taken, 2 mL $0.2 \times 10^{-4}$ mol/L DPPH solution was added, the mixture was mixed and reacted at room temperature in dark for 30 minutes, and methanol was then added to adjust final volume. The absorbance $A_i$ was measured at 517 nm. 2 mL control solution and 2 mL methanol were mixed, and the absorbance $A_j$ was measured. 2 mL DPPH solution and 2 mL methanol were mixed, and the absorbance $A_o$ was measured. The results are shown in Table 2.

TABLE 2

Absorbance

| Sample | Absorbance | Concentrations/(ppm) | | | | | | | | | |
|---|---|---|---|---|---|---|---|---|---|---|---|
| | | 1.76 | 8.80 | 21.12 | 42.24 | 79.20 | 112.64 | 281.60 | 492.80 | 792.00 | 915.20 |
| Vc | Ai | 0.799 | 0.703 | 0.183 | 0.103 | 0.089 | 0.070 | 0.065 | 0.065 | 0.063 | 0.058 |
| | Aj | 0.057 | 0.050 | 0.061 | 0.060 | 0.052 | 0.050 | 0.050 | 0.056 | 0.058 | 0.050 |
| | Ao | 0.943 | | | | | | | | | |
| A | Ai | 0.769 | 0.721 | 0.594 | 0.323 | 0.249 | 0.159 | 0.136 | 0.098 | 0.072 | 0.073 |
| | Aj | 0.064 | 0.049 | 0.040 | 0.045 | 0.042 | 0.039 | 0.061 | 0.057 | 0.043 | 0.048 |
| | Ao | 0.880 | | | | | | | | | |
| B | Ai | 0.792 | 0.754 | 0.703 | 0.620 | 0.514 | 0.472 | 0.378 | 0.263 | 0.223 | 0.220 |
| | Aj | 0.056 | 0.036 | 0.043 | 0.047 | 0.042 | 0.035 | 0.060 | 0.044 | 0.032 | 0.064 |
| | Ao | 0.806 | | | | | | | | | |

(d) The scavenging activity of the sample solution and control solutions is calculated according to the following calculation formula and shown in Table 3 and FIG. 3.

$$\text{Scavenging activity (\%)} = 100 \times [1 - (A_i - A_j)/A_o]$$

TABLE 3

DPPH Radical Scavening Activity

| Concentration/ (ppm) | Scavenging Activity (%) (n = 3) | | |
|---|---|---|---|
| | Vc | A | B |
| 1.76 | 21.35 | 19.87 | 8.69 |
| 8.80 | 30.80 | 23.68 | 10.97 |
| 21.12 | 87.03 | 37.02 | 18.10 |
| 42.24 | 95.44 | 68.43 | 28.89 |
| 79.20 | 96.06 | 76.52 | 41.44 |
| 112.64 | 97.88 | 86.33 | 45.83 |
| 281.60 | 98.41 | 91.48 | 60.58 |
| 492.80 | 99.04 | 95.31 | 72.81 |

TABLE 3-continued

DPPH Radical Scavenging Activity

| Concentration/ (ppm) | Scavenging Activity (%) (n = 3) | | |
|---|---|---|---|
| | Vc | A | B |
| 792.00 | 99.42 | 96.66 | 76.35 |
| 915.20 | 99.16 | 97.14 | 80.61 |

As shown in Tables 1-3 and FIG. 1, dihydroxytyrosol hexamethylene-1,6-dicarbamate (A) has obvious DPPH radical scavenging activity in a concentration dependent manner. Specifically, the DPPH radical scavenging activity ranges from 19.87% at 1.76 ppm to 97.14% at 915.20 ppm. Dihydroxytyrosol hexamethylene-1,6-dicarbamate (A) has better DPPH radical scavenging activity than hydroxytyrosol (B) at same concentration. Hydroxytyrosol thiodipropionic acid ester (A) has similar DPPH radical scavenging activity to vitamin C. Accordingly, hydroxytyrosol thiodipropionic acid ester can be used a food and cosmetic antioxidant additive, and has a wide application prospect.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of preparing a compound of formula I:

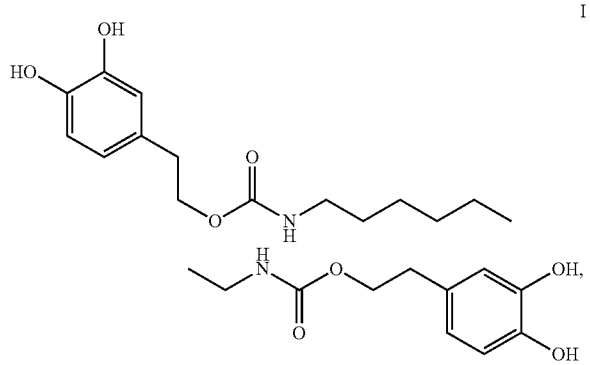

comprising:
reacting the compound of formula II with the compound of formula III to obtain the compound of formula I:

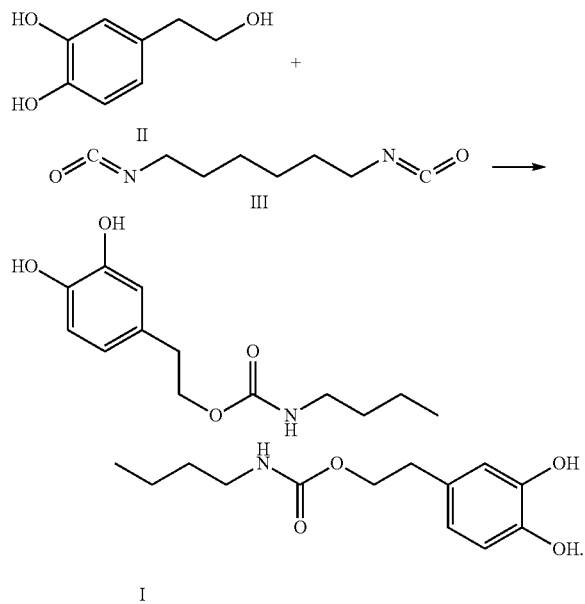

2. The method of claim 1, wherein the reaction of the compound of formula II with the compound of formula III comprises the following steps:

dissolving the compound of formula II and a catalyst in an organic solvent to form a reaction mixture under nitrogen atmosphere;
adding the compound of formula III to the reaction mixture;
heating the reaction mixture at 60-108° C. for 6-10 hours;
removing the organic solvent from the reaction mixture to obtain a crude product; and
purifying the crude product by silica gel flash chromatography with a mixture of petroleum ether and ethyl acetate as an eluent.

3. The method of claim 2, wherein the organic solvent is toluene, DMF, or acetonitrile.

4. The method of claim 3, wherein the organic solvent is toluene.

5. The method of claim 2, wherein the molar ratio of the compound of formula II and the compound of formula III is 2.5:1 to 3:1.

6. The method of claim 5, wherein the molar ratio of the compound of formula II and the compound of formula III is 3:1.

7. The method of claim 2, wherein the catalyst is triethylamine or DMAP.

8. The method of claim 7, wherein the catalyst is DMAP.

9. The method of claim 2, wherein the reaction mixture is heated at 108° C.

10. The method of claim 2, wherein the reaction mixture is heated for 8 hours.

11. The method of claim 2, wherein the mixture of petroleum ether and ethyl acetate has a volume ratio of 5:1.

* * * * *